(12) United States Patent
Netke et al.

(10) Patent No.: US 7,041,699 B2
(45) Date of Patent: May 9, 2006

(54) NUTRIENT PHARMACEUTICAL FORMULATION COMPRISING POLYPHENOLS AND USE IN TREATMENT OF CANCER

(75) Inventors: Shrirang Netke, Cupertino, CA (US); Aleksandra Niedzwiecki, San Jose, CA (US); Matthias Rath, Almelo (NL); Waheed M. Roomi, Sunnyvale, CA (US)

(73) Assignee: Matthias Rath, Santa Clara, CA (US)

( * ) Notice: Subject to any disclaimer, the term of this patent is extended or adjusted under 35 U.S.C. 154(b) by 0 days.

(21) Appl. No.: 10/342,044

(22) Filed: Jan. 13, 2003

(65) Prior Publication Data
US 2003/0170319 A1 Sep. 11, 2003

Related U.S. Application Data

(60) Provisional application No. 60/348,143, filed on Jan. 11, 2002.

(51) Int. Cl.
*A01N 43/16* (2006.01)
*A61K 31/35* (2006.01)

(52) U.S. Cl. .................. 514/456; 514/474; 424/682; 424/630; 424/639; 424/702

(58) Field of Classification Search ............. 514/474; 426/597, 591, 285, 477
See application file for complete search history.

(56) References Cited

U.S. PATENT DOCUMENTS

| | | | | |
|---|---|---|---|---|
| 5,817,695 A | * | 10/1998 | Pellico | 514/558 |
| 5,962,517 A | | 10/1999 | Murad | |
| 6,299,925 B1 | * | 10/2001 | Xiong et al. | 426/597 |
| 6,448,030 B1 | * | 9/2002 | Rust et al. | 435/29 |

FOREIGN PATENT DOCUMENTS

WO    WO 00/76492 A1    12/2000

OTHER PUBLICATIONS

U.S. Appl. No. 60/348,143, Netke et al., filed Jan. 2002.*
Chen L., et al., "Absorption Distribution, and Elimination of Tea Polyphenols in Rats" *Drug Metab. Dispos.* vol. 25, pp. 1045-1050 (1997).
Yang C.S., et al., "Blood and Urine Levels of Tea Catechins after Ingestion of Different Amounts of Green Tea by Human Volulenteers[1]" *Cancer Epidemol. Biomark. Prev.*, vol. 7, pp. 351-335 (1998).

(Continued)

*Primary Examiner*—Christopher S. F. Low
*Assistant Examiner*—Amy Lewis
(74) *Attorney, Agent, or Firm*—Kenyon & Kenyon

(57) ABSTRACT

A nutrient pharmaceutical formulation composition useful for treating cancer comprising ascorbic acid, L-lysine, L-proline and at least one polyphenol compound selected from the group consisting of epigallocatechin gallate, epicatechin gallate, epigallocatechin, epicatechin, catechin and the use of the composition in treating cancer and other tumors are provided.

2 Claims, 14 Drawing Sheets

OTHER PUBLICATIONS

Bell J.R., et al., "(+)-Catechin in human plasma after ingestion of a single serving of reconstituted red wine[1-3]" *Am. J. Clin. Nutr.*, vol. 71, pp. 103-108 (2000).

Chow, Sherry H.H., et al., "Phase I Pharmacokinetic Study of Tea Polyphenols following Single-dose Administration of Epigallocatechin Gallate and Polyphenon E[1]" *Cancer Epidemol. Biomark. Prev.*, vol. 10, pp. 53-58 (2001).

Mukhtar H. and Ahmad N., "Tea Polyphenols: prevention of cancer and optimizing health[1-3]" *Clin. Nutr.*, vol. 71, pp. 1698S-1702S (2000).

Ahmed N., et al., "Green Tea Constituent Epigallocatechin-3-Gallate and Induction of Apoptosis and Cell Cycle Arrest in Human Carcinoma Cells" *J. Natl. Cancer Inst.*, vol. 89, pp. 1881-1886 (1997).

Cao Y. and Cao R., "Angiogenesis inhibited by drinking tea" *Nature*, vol. 398, p. 381 (1999).

Jankun J. et al., "Why drinking green tea could prevent cancer" *Nature*, vol. 387, p. 561 (1997).

* cited by examiner

Effect of supplementation of Basal with 100μM ascorbic acid (AA), 140μM Proline (P), 400μM lysine (L) and various levels of epigallocatechin gallate (EGCG) on cell proliferation of melanoma A2058 cells.

Effect of epigallocatechin gallate (EGCG) on cell proliferation of breast cancer cells MDA-MB 231.

Effect of supplementation of Basal with 100μM ascorbic acid (AA), 140μM Proline (P), 400μM lysine (L) and various levels of epigallocatechin gallate (EGCG) on cell proliferation of breast cancer cells MDA-MB231

Effect of supplementation of Basal with 100μM ascorbic acid (AA), 140μM Proline (P), 400μM lysine (L) and various levels of epigallocatechin gallate (EGCG) on cell proliferation of colon cancer cells HCT116

Effect of supplementation of Basal with 100μM ascorbic acid (AA), 140μM proline (P), 400μM lysine (L) and various levels of epigallocatechin gallate (EGCG) on expression of matrix metalloproteinases (MMP) by melanoma cells.
1. Markers; 2.Basal; 3.AA+P+L; 4.EGCG 10μg/ml; 5.AA+P+L+10μg/mlEGCG;6.EGCG 20μg/ml; 7.AA+P+L+EGCG 20μg/ml; 8.EGCG 50μg/ml; 9.AA+P+L+EGCG 50μg/ml Effect of supplementation of Basal with 100μM ascorbic acid (AA), 140μM Proline (P), 400μM lysine (L) and various levels of epigallocatechin gallate (EGCG) on Matrigel invasion by breast cancer cells MDA-MB 231

Effect of supplementation of Basal with 100μM ascorbic acid (AA), 140μM Proline (P), 400μM lysine (L) and various levels of epigallocatechin gallate (EGCG) on Matrigel invasion by colon cancer cells HCT116.

Effect of supplementation of Basal with 100µM ascorbic acid (AA), 140µM Proline (P), 400µM lysine (L) and various levels of epigallocatechin gallate (EGCG) on Matrigel.

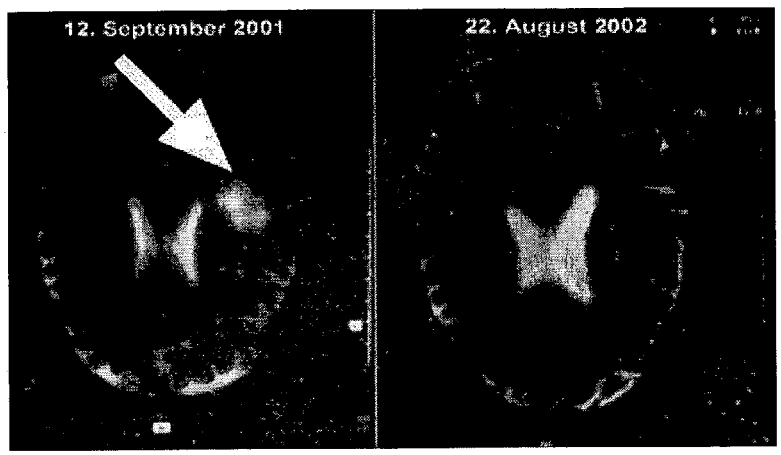
Figure 13 depicts MR scans of a female patient diagnosed with Gliablastoma after suffering a facial stroke. The left diagram reveals a brain tumor on the left side of the brain. The right diagram reveals that the brain tumor disappeared after the administration of EPICAN FORTE™

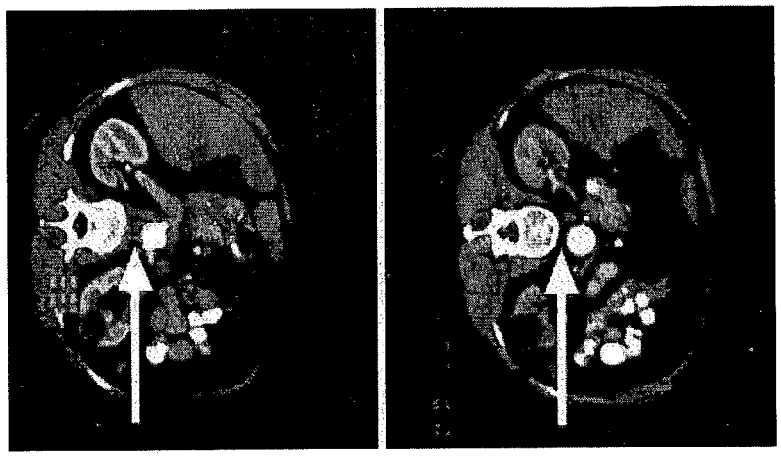
Figure 14 depicts X-ray CT scans of a male patient diagnosed with prostate cancer. The left diagram reveals metastasis along the lymphatic vessels of the aorta. The right diagram reveals that the lymphatic metastasis was not detectable and that the patient's prostate gland returned to normal size after the administration of EPICAN FORTE™.

NUTRIENT PHARMACEUTICAL FORMULATION COMPRISING POLYPHENOLS AND USE IN TREATMENT OF CANCER

CROSS-REFERENCE TO RELATED APPLICATION

This application claims the benefit under 35 U.S.C. § 119(e) of U.S. provisional applications Ser. No. 60/348,143 filed Jan. 11, 2002, the content of which is incorporated herein by reference in its entirety

FIELD OF THE INVENTION

The present invention relates to a nutrient pharmaceutical formulation and its use for the treatment of cancer. More specifically, the present invention relates to polyphenol containing pharmaceutical formulations having an effective amount of polyphenols for the treatment of cancer. The formulation of the present invention is used as an agent for the prevention and treatment of cancer comprising ascorbic acid, lysine, proline and at least one polyphenol compound selected from the group consisting of epigallocatechin gallate, epicatechin gallate, epigallocatechin, epicatechin, and catechin.

BACKGROUND OF THE INVENTION

Cancer is one of the leading causes of death in the industrialized world. There exists no specific and causal treatment for cancer and mortality from cancer is among the highest from all diseases. The most widely used treatments—chemotherapy and radiotherapy—do not distinguish between healthy tissue and cancer and are associated with severe side effects. Thus, there is a need for a selective treatment of cancer.

One of the key mechanisms that cancer cells use in order to expand and metastasize in the body involves enzymatic destruction of the surrounding connective tissue. Therapeutic approaches to control this process through specific drugs have not been successful and currently there are no means available to control cancer metastasis. Current treatment protocols with chemotherapy and radio-therapy focus on cancer cell destruction in the body, and they do not address metastasis. Moreover, these treatments are toxic, not specific and associated with severe side effects. Chemotherapy and radio-therapy carry a risk of the development of new cancers and through their destruction of connective tissue in the body can facilitate the invasion of cancer.

In order to grow and expand to other parts of the body, cancer cells degrade the extracellular matrix through various matrix metalloproteinases (MMPs) and plasmin, whose activities have been correlated with an aggressiveness of tumor growth. Rath and Pauling (1992) postulated that nutrients such as an amino acid, lysine and ascorbic acid can act as natural inhibitors of extracellular matrix proteolysis and as such they have the potential to modulate tumor growth and expansion. These nutrients can exercise their anti-tumor potential through several mechanisms, among them by inhibition of MMPs and by strengthening of the connective tissue surrounding cancer cells (tumor "encapsulating" effect).

U.S. Pat. No. 5,962,517 discloses a pharmaceutical composition for a different medical indication (acne treatment). The disclosed composition comprises an acne reduction component, at least one of burdock root yellow dock root, or a catechin-based composition; and a skin cell conditioning component comprising a transition metal. The disclosed composition is not shown to have any beneficial value in cancer treatment and/or prevention.

PCT WO 00/76492 discloses a nutrient formulation for disease reduction that contains a catechin compound. However, the bioavailability of catechin compounds has been shown to be small low (Chen L., Lee M. J., Yang C. S. Drug Metab. Dispos. 25: 1045–1050 (1997); Yang C. S., Chen L., Lee M. J., Balentine D. A., Kuo M. C., Schantz S. Cancer Epidemol. Biomark. Prev. 7: 351–35 (1998); Bell J. R., Donovan J. L., Wong R., Waterhouse H., German J. B., Walzem R. L., Kasim K. Am. J. Clin. Nutr. 71:103–108 (2000); Sherry Chow H. H., Cai Y., Alberts D. S., Hakim I., Dorr R., Shahi F., Crowell J. A., Yang S. C., Hara H. Cancer Epidemol. Biomark. Prev. 10: 53–58 (2001)) and the PCT WO 00/76492 fails to disclose a means to increase the bioavailability as is required in cancer treatment and/or prevention.

Demeule et al. discloses that green tea catechins may have inhibitory effects on matrix metalloproteinase. There is no suggestion or teaching regarding how to use catechins in cancer treatment and/or prevention. Given the fact that the bioavailability of polyphenols in humans is extremely low, the low tissue concentration of catechins greatly reduces the therapeutic value of polyphenols including epigallocatechin gallate (EGCG). There is a constant need in finding a better nutrient pharmaceutical composition containing polyphenols that is effective in the treatment of neoplastic diseases and other diseases including inflammatory diseases.

There is a need for safe and effective natural approaches that can be used to control the process of cancer expansion in the body. There is also a need for a preventive measure against cancers or benign tumors to develop in human and such measure could be applied to patients without the risk of treatment-related side effects. Nutrient pharmaceutical compositions have become popular, as the incidence of cancer in recent time increases. The requirement of such composition will continue and will likely increase.

SUMMARY OF THE INVENTION

In one object, the present invention provides a nutrient pharmaceutical composition useful in treating cancer, comprising: a) an ascorbic compound, b) a L-lysine compound, c) a L-proline compound, and d) at least one polyphenol compound selected from the group consisting of epigallocatechin gallate, epicatechin gallate, epigallocatechin, epicatechin, and catechin. Compounds of a–c) enhance the polyphenol compound's activity in blocking cancer proliferation and metastasis.

Preferably, the ascorbic compound is selected from the group consisting of ascorbic acid, pharmaceutical acceptable ascorbate salts, ascorbate esters and/or mixture thereof. Preferably, the pharmaceutical acceptable ascorbate salt is calcium ascorbate or magnesium ascorbate. More preferably, the ascorbate ester is ascorbyl palmitate. Preferably, the lysine compound is selected from the group consisting of lysine hydrochloride and lysine pharmaceutically acceptable lysine salts. Preferably, the proline compound is selected from the group consisting of proline hydrochloride and proline pharmaceutical acceptable proline salts.

In another object, the present nutrient pharmaceutical composition further comprises a trace element selected from the group consisting of selenium, copper, manganese, calcium and magnesium.

In another object, the present nutrient pharmaceutical composition further comprises an amino acid. Preferably, the amino acid is arginine. More preferably, the present nutrient pharmaceutical composition further comprises N-acetyl cysteine.

In another object, the present invention provides a nutrient pharmaceutical composition useful in treating cancer, comprising: a) an ascorbic compound, b) a L-lysine compound, c) a L-proline compound, d) N-acetyl cysteine, and e) at least one polyphenol compound selected from the group consisting of epigallocatechin gallate, epicatechin gallate, epigallocatechin, epicatechin, and catechin. The a–d) compounds enhance the polyphenol compound's activity in blocking cancer proliferation and metastasis.

In another object, the present invention provides a nutrient pharmaceutical composition comprising 250 mg ascorbic acid, 250 mg calcium ascorbate, 250 mg magnesium ascorbate, 250 mg ascorbyl palmitate, 1,000 mg polyphenols, 200 mg N-acetyl-cysteine, 1,000 mg lysine, 750 mg proline, 500 mg arginine, 30 mcg selenium, 2 mg copper, and 1 mg manganese.

In another object, the present invention provides a nutrient pharmaceutical composition comprising 25 mg ascorbic acid, 25 mg calcium ascorbate, 25 mg magnesium ascorbate, 25 mg ascorbyl palmitate, 200 mg polyphenols, 10 mg N-acetyl-cysteine, 50 mg lysine, 25 mg proline, 50 mg arginine, 1 mcg selenium, 20 mcg copper, and 50 mcg manganese.

In another object, the present invention provides a nutrient pharmaceutical composition comprising 5,000 mg ascorbic acid, 5,000 mg calcium ascorbate, 5,000 mg magnesium ascorbate, 5,000 mg ascorbyl palmitate, 5,000 mg polyphenols, 1,500 mg N-acetyl-cysteine, 5,000 mg lysine, 3,000 mg proline, 3,000 mg arginine, 200 mcg selenium, 9 mg copper, and 10 mg manganese.

In another object, the present invention provides a nutrient pharmaceutical composition comprising 250 mg ascorbic acid, 250 mg calcium ascorbate, 250 mg magnesium ascorbate, 250 mg ascorbyl palmitate, 1,000 mg polyphenols, 200 mg N-acetyl-cysteine, 1,000 mg lysine, 750 mg proline, 500 mg arginine, 100 mcg selenium, 2 mg copper, 1 mg manganese, 500 mg calcium, and 400 mg magnesium.

In another object, the present invention provides a nutrient pharmaceutical composition comprising 250 mg ascorbic acid, 250 mg calcium ascorbate, 250 mg magnesium ascorbate, 250 mg ascorbyl palmitate, 1,000 mg polyphenols, 200 mg N-acetyl-cysteine, 1,000 mg lysine, 750 mg proline, 500 mg arginine, 100 mcg selenium, 2 mg copper, 1 mg manganese, 500 mg calcium, 400 magnesium, and 200 citrus biofavonoids.

In yet another object, the present invention provides a nutrient pharmaceutical composition useful in treating cancer, comprising: L-lysine, L-proline, L-arginine, ascorbic acid, calcium, magnesium, polyphenols, N-acetyl-cysteine, selenium, copper, and manganese.

In another object, the present invention provides a nutrient pharmaceutical composition comprising 1,000 mg L-lysine, 750 mg L-proline, 500 mg L-arginine, 710 mg ascorbic acid, 22 mg calcium, 50 mg magnesium, 1,000 mg polyphenols, 200 mg, N-acetyl cysteine, 30 mcg selenium, 2 mg copper, and 1 mg manganese.

In another object, the present invention provides a method of treating cancer in an individual, comprising the step of administering to the individual the nutrient pharmaceutical compositions as disclosed. Preferably, the cancer is selected from the group consisting of melanoma cancer, breast cancer, colon cancer, lung cancer and brain cancer.

In another object, the present invention provides a method of treating an inflammatory disease in an individual, comprising the step of administering to the individual the nutrient pharmaceutical composition as disclosed. Preferably, the inflammatory disease is osteoarthritis.

BRIEF DESCRIPTION OF DRAWINGS

FIG. 13 depicts MR scans of a female patient diagnosed with Gliablastoma after suffering a facial stroke. The left diagram reveals a brain tumor on the left side of the brain. The right diagram reveals that the brain tumor disappeared after the administration of EPICAN FORTE™.

FIG. 14 depicts X-ray CT scans of a male patient diagnosed with prostate cancer. The left diagram reveals metastasis along the lymphatic vessels of the aorta. The right diagram reveals that the lymphatic metastasis was not detectable and that the patient's prostate gland returned to normal size after the administration of EPICAN FORTE™.

DETAILED DESCRIPTION OF THE INVENTION

Figure 1:
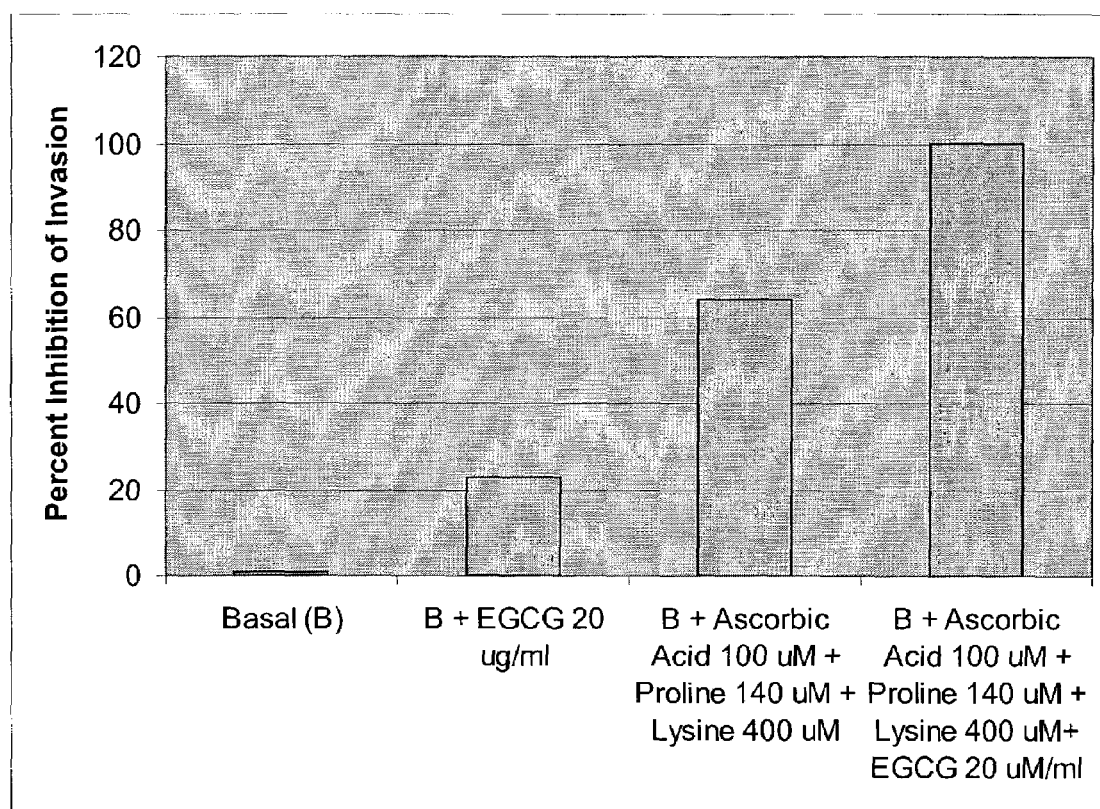
FIG. 1 depicts the inhibitory effects of polyphenols, ascorbate, proline and lysine on migration behavior of human breast cancer cells.

As used herein, "lysine" is used interchangeable with L-lysine, "proline" is used interchangeable with L-proline, "arginine" is used interchangeable with "L-arginine"; "vitamin C" is used interchangeable with ascorbic acid, and may include ascorbate salts or ascorbate esters. "MMPs" refers to matrix metalloproteinases; e.g., MMP-1, MMP-2, MMP-3, MMP-4, MMP-5, MMP-6, MMP7, MMP-8, MMP-8, MMP-9, MMP-10, MMP-11 etc. "EGCG" refers to (–)-epigallocatechin-3-gallate which is the major polyphenolic constitutents present in green tea. "NHDF" refers to normal human dermal fibroblast, including human chondrocytes and human stromal cells.

The present invention provides a nutrient pharmaceutical composition ascorbic acid, lysine, proline and at least one polyphenol compound. Preferably, ascorbate compound is selected from the group consisting of ascorbic acid, ascorbate salts and ascorbate esters. Preferably, lysine is lysine hydrochloride or pharmaceutically acceptable lysine salts. Preferably, proline is proline hydrochloride or pharmaceutically acceptable proline salts thereof.

Polyphenol compounds are extracts of green tea. They are also known as catecins. Polyphenols are present in green tea and have been suggested to provide protection against variety of illnesses including cancer (Mukhtar H., Ahmed N. Am. J. Clin. Nutr. 71:1698S–1702S (2000)). Oral administration of green tea enhanced the tumor-inhibitory effects of doxorubicin in mice. The potential anti-cancer activity of catechins may relate to their effects on several factors involved in proliferation of cancer cells and their metastasis. Catechins are known to cause cell cycle arrest in human carcinoma cells (Ahmad N., Feyes D. K., Nieminen A. L., Agarwal R., Mukhtar H. J. Natl. Cancer Inst. 89: 1881–1886 (1997)). Polyphenolic fraction from green tea is also implicated to protect against inflammation and cytokines induced by tumors.

Polyphenolic compounds present as 30% dry weight in green tea. They include flavanols, flavandiols, flavonoids, and phenolic acids. Flavanols are the most abundant among the polyphenols in green tea and are commonly known as catechins. There are four major catechins in green tea: 1) (–)-epicatechin, 2) (–)-epicatechin-3-gallate, 3) (–)-epigallocatechin, and 4) (–)-epigallocatechin-3-gallate (EGCG). Among the catechins, EGCG is the major polyphenolic constitutents present in green tea. EGCG is a potent antioxidant compound and may attribute to the anti-cancer activity of green tea. Catechin compounds were reported to exercise its anti-metastatic activity by preventing the angiogenesis process (Cao Y., Cao R. Nature 398:381 (1999)). EGCG has also been shown to interfere with the activity of urokinase (u-plasminogen activator) (Jankun J., Selman S. H., Swiercz R., Skrzypczak J. E. Nature: 387–567 (1997)), one of the most frequently expressed enzymes in human cancers. EGCG is a preferred polyphenol compound.

Preferably, polyphenol compound is selected from the group consisting of epigallocatechin gallate, epicatechin gallate, epigallocatechin, epicatechin, catechin and other pharmaceutically acceptable polyphenol salts and/or mixtures thereof.

One of the main therapeutic target of this patent application is the prevention of the digestion of the extracellular matrix and its restoration. Ascorbic acid or its salt (i.e., ascorbate) is required for the synthesis of collagen, elastin and other key extracellular matrix molecules.

Preferably, a combination of ascorbic acid, proline and lysine is used to enhance the anti-cancer activity of polyphenol compounds. More preferably, the combination enhances the polyphenol compounds including epigallocatechin gallate, epicatechin gallate, epigallocatechin, epicatechin, catechin in such a manner that the polyphenol compound is effective in reducing invasion of cancer cells or completely blocking the invasion.

Without bound by any theory, the present nutrient pharmaceutical formulation contains a mixture of ingredients including polyphenols and the mixture is found to function effectively in blocking proliferation and metastasis processes. We found that the present nutrient formulation composition significantly reduces the invasion of cancer cells or blocks the metastasis of cancer cells completely. Thus, this composition effectively prevented these cancer cells from spreading. The therapeutic use of the compound claimed is an effective, selective and safe treatment for cancer of the breast, colon and of other organs. Preferably, the disclosed nutrient pharmaceutical composition may contain two of the components that are covalently bound.

Preferably, the efficacy of the nutrient composition is enhanced by including compounds known to beneficially affect growth and invasion of cancer and other tumors, including L-arginine and/or arginine-containing compounds. More preferably, N-acetyl-cysteine is used. More preferably, a selenium salt, a copper salt, and a manganese salt are used that are effective to prevent and treat cancer and other tumors. This composition may also include one or more compounds needed as a coenzyme in the Krebs-Cycle, the respiration chain, or for other metabolic functions of cells in an amount effective to prevent and treat cancer and other tumors.

The present nutrient pharmaceutical composition may be administered to a patient in form of capsules, tablets, powders, pills, injections, infusions, inhalations, suppositories or other pharmaceutically acceptable carriers and/or means of delivery for the prevention and treatment of cancer and other tumors. Preferably, the nutrient pharmaceutical composition is administered as capsules, tablets or powders. More preferably, it is administered as capsules.

The present nutrient pharmaceutical composition can be used in preventing and treating cancer and other tumors in a selected patient where the tumor or cancer is located in the breast, ovaries, cervix or other organs of the female reproductive system, lung, liver, skin, gastrointestinal system, brain, bones or other organs of the body. Preferably, the composition is used in lung cancer and brain cancer.

The present nutrient pharmaceutical composition can also be used in preventing and treating the infectious diseases, atherosclerosis, restenosis, other cardiovascular diseases and inflammatory diseases. Preferably, the inflammatory disease is osteoarthritis.

MMP-Mediated Plasmin Activation: It is speculated that MMPs activity can be affected by lysine through plasmin-mediated mechanisms although other mechanisms are not excluded. The MMPs are secreted as proenzymes and their activation is mediated partially by plasmin and its completion requires active form of MMP-3. The mechanism of activation of various MMPs detailed by Nagase (1997) indicates that MMP-3 also requires the conversion of plasminogen to its active form, plasmin. Plasminogen active binding center has the sites where lysine gets specifically attached. Therefore lysine can interfere with activation of plasminogen into plasmin by plasminogen activator (Rath and Pauling, 1992), by binding to plasminogen active sites. tranexamic acid, a synthetic lysine analog has been used to inhibit plasmin induced proteolysis through this mechanism.

Since plasmin activity is essential to induce several tissue MMPs, lysine can interfere with conversion of plasminogen to plasmin and thereby it can inhibit the activation of almost all MMPs. In addition, EGCG may exert an inhibitory effect on extracellular matrix degradation through inhibition of MMP-2.

Cancer Invasion and Role of Matrix: It is also possible to affect cancer cell matrix invasion by increasing the stability and strength of the connective tissue surrounding cancer cells, and contributing to the "encapsulation" of the tumor. This requires optimizing the synthesis and structure of collagen fibrils, for which the hydroxylation of hydroxyproline and hydroxylysine residues in collagen fibers is essential. Ascorbic acid may be essential for hydroxylation of these amino acids. Ascorbic acid and L-lysine are not normally produced in the human body; therefore, suboptimal level of these nutrients is possible in various pathological stages as well as through inadequate diets. Although proline can be synthesized from arginine, its synthesis and or hydroxylation may be affected at pathological conditions. As such, it has been shown that hydroxyproline content of metastatic tumor tissue is much lower than non-metastatic tumor tissue (Chubainskaia et al., 1989). A variety of drugs that reduced metastasis also increased the hydroxyproline content of the tissues (Chubinskaia et al., 1989). The urinary hydroxyproline content of cancer patients has been found to be higher than that in healthy persons or non-cancer patients (Okazaki et al., 1992). All these findings suggest adverse effects of cancer cells on metabolism of proline and possible conditioned deficiency of proline in cancer patients.

Cancer patients may have insufficient levels of ascorbic acid. Ascorbic acid may be cytotoxic to malignant cell lines and exerts anti-metastatic action. The present invention discloses that a combination of ascorbic acid, proline, lysine and at least one poyphenol compound exerts a potent anti-proliferative and anti-metastatic effect on cancer cell lines. Preferably, the present nutrient pharmaceutical formulation is effective against melanoma, breast cancer and colon cancer cells. Most preferably, the present pharmaceutical formulation is effective against human colon cancer cells.

Polyphenol Compounds (Catechins): EGCG represents one of the catechins in green tea extract and may have growth inhibitory effects against human cancer cells. The exact underlying mechanism is unclear. The present invention discloses a surprising synergy in the nutrient pharmaceutical formulation comprising ascorbic acid, proline and lysine and at least one polyphenol compound in effectively blocking proliferation and metastasis of cancer cells.

The nutrient pharmaceutical composition of the present invention effectively block the invasion of cancer of the breast, colon, skin (melanoma), and other forms of cancer. The ingredients present in the nutrient formulation are naturally occurring compounds; and when used in the claimed range as disclosed in the application, they are shown to have no toxic side effects. Thus, this composition can also be used prophylactically, i./e. the effective prevention of cancer and other tumors in the body.

Since viral cells and other invasive microorganisms use similar proteases that cancer cells for spreading of the infection through the body, the composition claimed in this patent may be used in the effective prevention and treatment of viral diseases and other infectious diseases.

Similar mechanism of activation of matrix metalloproteinases that cancer cells use for matrix invasion also contributes to destabilization of atherosclerotic plaques leading to myocardial infarctions and stroke. Therefore, the composition claimed in this patent can also be used in the effective prevention and treatment of atherosclerosis, restenosis and other cardiovascular complications.

Activation of matrix metalloproteinases that cancer cells use for matrix invasion is a key component in various inflammatory conditions. Therefore, the composition claimed in this patent can also be used in the effective prevention and treatment of diseases, such as rheumatoid arthritis, emphysema, allergies, osteoarthritis and other conditions that include inflammatory aspects.

The nutrient pharmaceutical composition of the present invention can be provided to a patient in form of tablets, pills, injections, infusions, inhalations, suppositories or other pharmaceutically acceptable carriers and/or means of delivery.

EXAMPLES

The effects of ascorbic acid, lysine, proline, and at least one polyphenol compound were studied for their anti-proliferative and anti-invasive potential in various human cancer cell lines. More particularly, one of the green tea extract ingredient (i.e., epigallochatechin gallate (EGCG)) was examined.

Materials and Methods

Human breast cancer cells MDA-MB-231, human colon cancer cells HCT 116, human melanoma cell line A2058 were obtained from ATCC. Normal human dermal fibroblasts were obtained from GICBO. Where not indicated, the culture media obtained from ATCC were used.

In cancer cell proliferation studies each treatment was replicated eight times. In the invasion assays, each treatment was performed in three or four replicates.

Cell Proliferation Studies

In these studies $5 \times 10^4$ breast cancer cells were grown in Liebovitz's medium with 10% fetal bovine serum (FBS) in 24-well plates. The medium was used as such (basal) or with designated supplements. Plates were incubated in an air-circulating incubator (without supplemental $CO_2$) for four days. The colon cancer cells HCT116 were grown in McCoy's 5A media and maintained in a 5% $CO_2$-air circulating incubator. At the end of the incubation period, the media were withdrawn and the cells in the wells were washed with PBS followed by incubation for 3 hours with MTT stain. Dimethyl-sulfoxide (DMSO, 1 ml) was added to each well. The plates with DMSO were allowed to stand at room temperature for 15 minutes with gently agitation and then OD of the solution in each well was measured at 550 nm. The $OD_{550}$ of the DMSO solution in the well was considered to be directly proportional to the number of cells. The $OD_{550}$ of treatment that did not contain any supplement (Basal) was considered as 100.

Matrigel Invasion Studies

The studies were conducted using Matrigel (Becton Dickinson) inserts in compatible 24-well plates. Fibroblasts were seeded and grown in the wells of the plate using DMEM. When fibroblasts reached confluence, the medium was withdrawn and replaced with 750 μl of the media designated for the treatment. The cancer cells ($5 \times 10^4$) suspended in 250 μl of the medium supplemented with nutrients as specified in the design of the experiment were seeded on the insert in the well. Thus both the medium on the insert and in the well contained the same supplements. The plates with the inserts were then incubated (in air-circulating incubator for MDA-MB-231 cells and 5% $CO_2$ incubator for colon cancer cells and melanoma cells) for 18–20 hours. After incubation, the media from the wells was withdrawn. The cells on the upper surface of the inserts were gently scrubbed away with cotton swab. The cells that had penetrated the Matrigel membrane and had migrated on the lower surface of the Matrigel were stained with hemacolor stain (EM Sciences) and were visually counted under the microscope. The results were subjected to ANOVA and all the possible pairs were tested for significance at p<0.05.

The media in different studies were supplemented with ascorbic acid, proline, lysine and EGCG at concentrations as indicated.

Gelatinase Zymography

Gelatinase zymography was performed in 10% Novex pre-cast polyacrylamide gel (Invitrogen) in the presence of 0.1% gelatin. Culture media (20 µl) was loaded and SDS-PAGE was performed with tris-glysine SDS buffer. After electrophoresis, the gels were washed with 5% Triton X-100 for 30 minutes and stained. Protein standards were run concurrently and approximate molecular weights were determined.

Example 1

MDA-MB 231 (ATCC) breast cancer cells were seeded on Matrigel insert in an improved Matrigel Invasion Chamber (BD). Conditioned media from normal human dermal fibroblast (Clonetics) supplemented with various agents (as indicated on FIG. 1) were added to the well. The chamber was incubated for 24 hours and the cells that had invaded the Matrigel membrane and had migrated into the lower surface of the membrane were counted. These data show the inhibitory effect of epigallocatechin gallate and the combination of ascorbic acid, proline and lysine on Matrigel invasion and migration by MDA-MB 231 human breast cancer cells. These data also show that the combined effects of ascorbic acid, proline and lysine in enhancing the anti-cancer activity of epigallocatechin gallate.

Example 2

Figure 2:
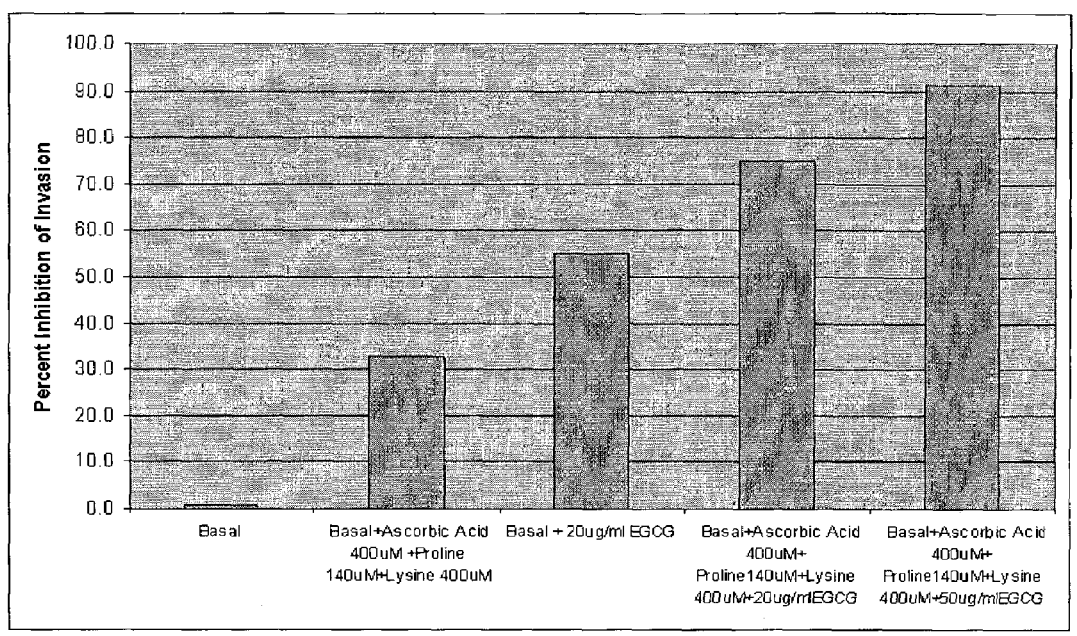
FIG. 2 depicts the inhibitory effects of polyphenols, ascorbate, proline, and lysine on migration behavior of human colon cancer cells.
Figure 3:
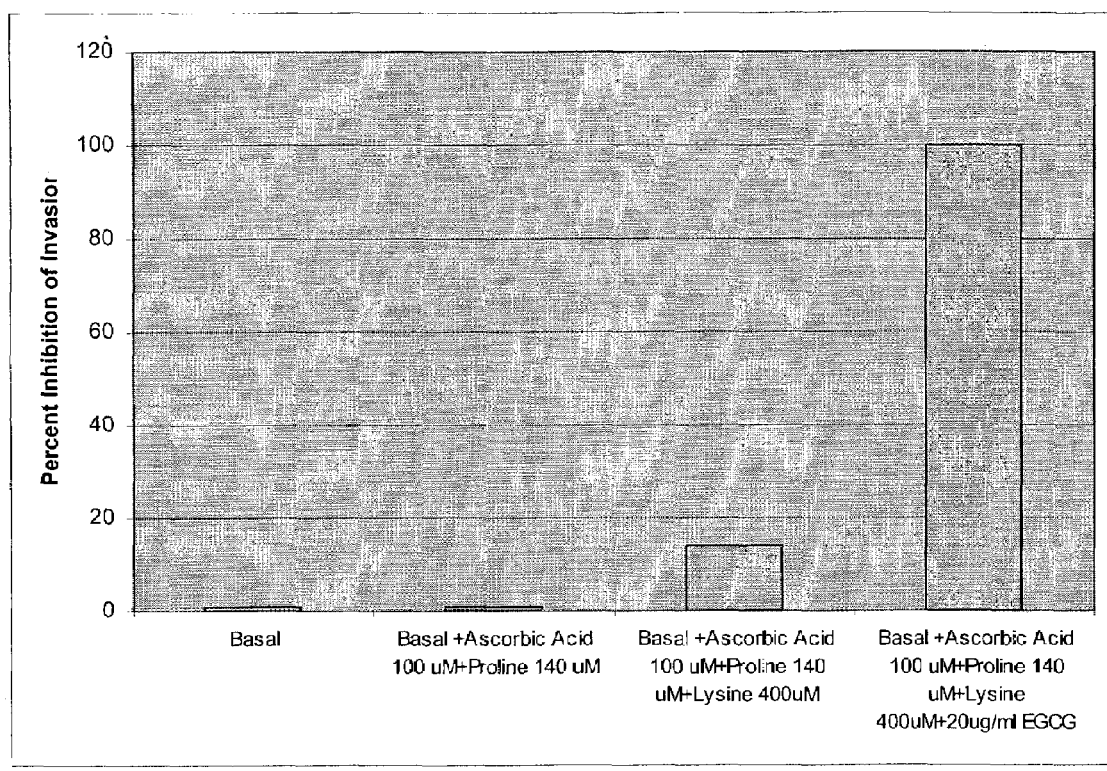
FIG. 3 depicts the inhibitory effects of polyphenols, ascorbate, proline, and lysine on migration behavior of human melanoma cells.

HTCT116 (ATCC) human colon cancer cells were seeded on Matrigel insert in an improved Matrigel Invasion Chamber (BD). Conditioned media from Normal Human Dermal Fibroblast (Clonetics) supplemented with various agents (as indicated on FIG. 2) were added to the well. The chamber was incubated for 24 hours and the cells that had invaded the Matrigel membrane and had migrated into the lower surface of the membrane were counted. These data show an inhibitory effect of epigallocatechin gallate and the combination of ascorbic acid, proline and lysine on Matrigel invasion and migration by HCT116 human colon cancer cells. These data also show that the combined effects of ascorbic acid, proline and lysine in enhancing the anti-cancer activity of epigallocatechin gallate.

Example 3

A2058 (ATCC) human melanoma cells were seeded on Matrigel insert in improved Matrigel Invasion Chamber (BD). Conditioned media from Normal Human Dermal Fibroblast (Clonetics) supplemented with various agents was added to the well. The chamber was incubated for 24 hours and the cells that had invaded the Matrigel membrane and had migrated into the lower surface of the membrane were counted. These data show an inhibitory effect of epigallocatechin gallate and the combination of ascorbic acid, proline and lysine on Matrigel invasion and migration by A2058 human melanoma cells. These data also show that the combined effects of ascorbic acid, proline and lysine in enhancing the anti-cancer activity of epigallocatechin gallate.

Example 4

In this experiment A2058 (ATCC) human melanoma cells were seeded on Matrigel insert in an improved Matrigel Invasion Chamber (BD) in the presence of:

A: conditioned media from Normal Human Dermal Fibroblast (Clonetics) and

Figure 4:
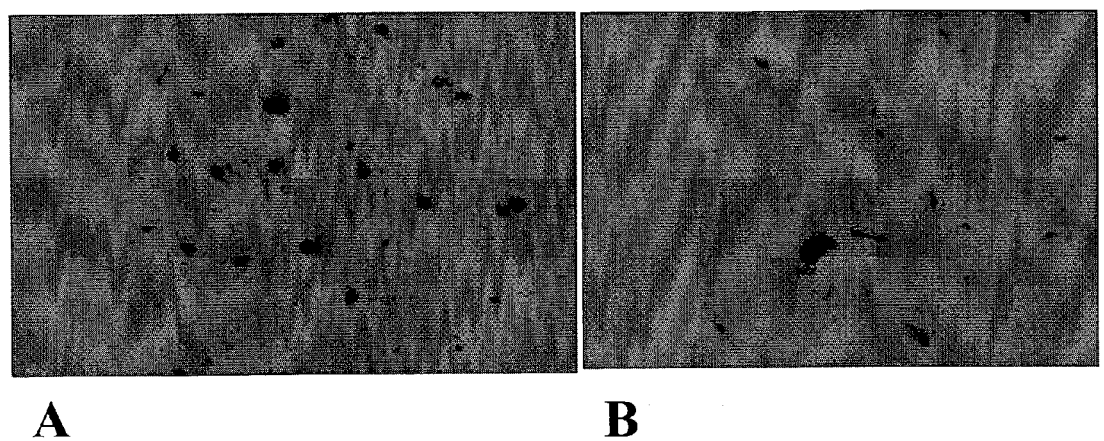
FIG. 4 depicts the inhibitory effects of polyphenol, ascorbate, proline, and lysine on apoptosis of human melanoma cells.

B: the same media supplemented with various nutrients as indicated in the FIG. 4 legends. After 24 hours of incubation the cells that invaded the Matrigel membrane and migrated to the lower surface of the membrane were examined under the microscope and counted.

These data show an apoptotic effect of epigallocatechin gallate and the combination of ascorbic acid+proline+lysine on A2058. A; Human Melanoma Cells in tissue culture medium. B: Human Melanoma Cells in tissue culture medium containing ascorbic acid (100 µM), proline (140 µM), lysine (400 µM) and EGCG (20 µg/ml). Note: the cells were destroyed. These data also show that the combined effects of ascorbic acid, proline and lysine in enhancing the anti-cancer activity of epigallocatechin gallate.

Example 5

Cancer Cells Proliferation Study

Melanoma A2058 Cells

Figure 5:
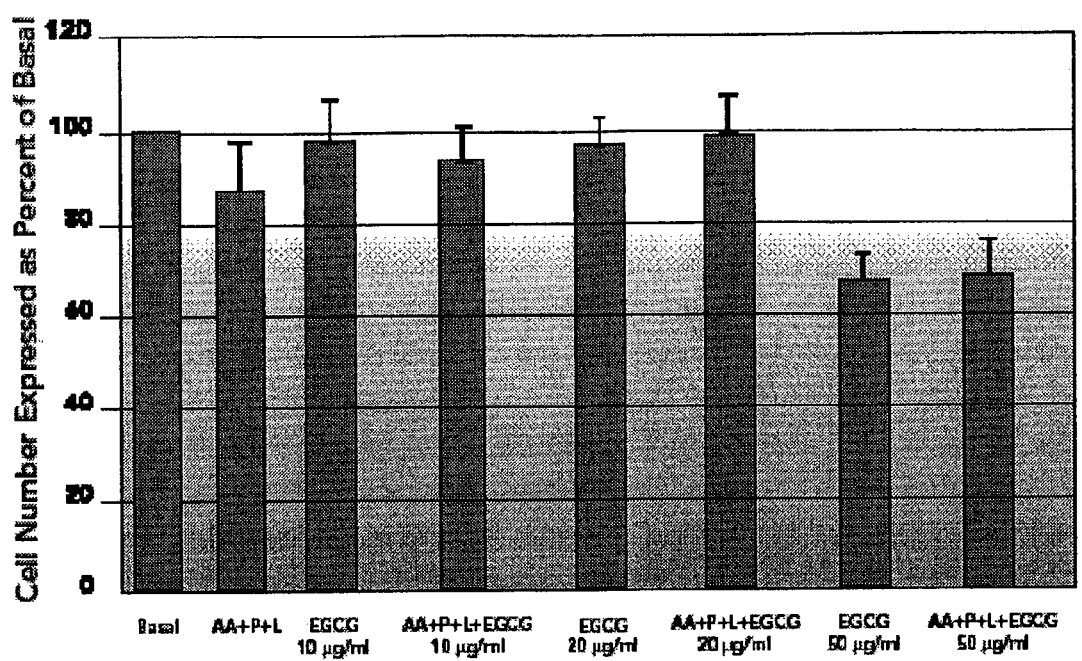
FIG. 5 depicts the inhibitory effects of ascorbic acid, proline, lysine and various amounts of EGCG on cell proliferation of human melanoma cells (A 2058).

FIG. 5 shows the effect of 10, 20 and 50 µg/ml of EGCG without and with lysine, proline, and ascorbic acid supplementation on the proliferation of melanoma cells. Neither lysine, proline, and ascorbic acid nor EGCG at 10 and 20 µg/ml had any significant effect on cell proliferation. However, EGCG at 50 µg/ml significantly reduced the cell number to 30%. A similar effect was observed with lysine, proline and ascorbic acid.

Breast Cancer MDA-MB-231 Cells

Figure 6:
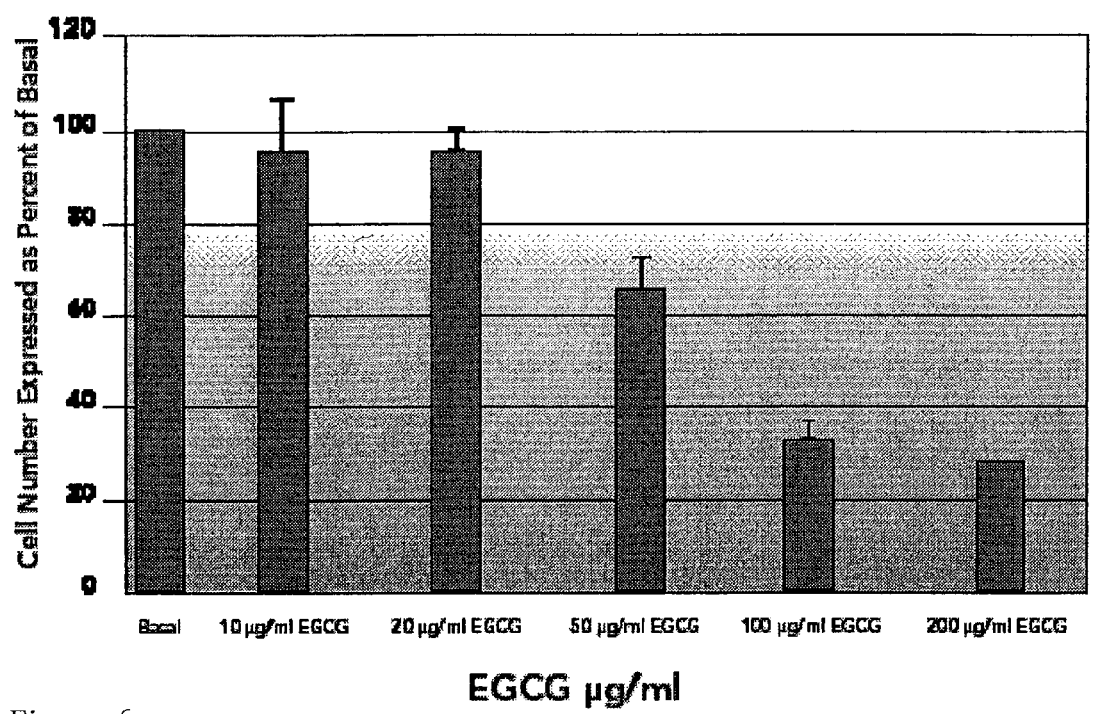
FIG. 6 depicts the inhibitory effects of EGCG on cell proliferation of human breast cancer cells (MDA-MB 231).

In these experiments, the basal media was supplemented with 0, 10, 20, 50,100 or 200 µg/ml of EGCG (FIG. 6). The results show that supplementation of the basal media with 50, 100 and 200 µg/ml of EGCG significantly reduced the cell number to 66.1±5.3, 33.6±2 and 29.6±0.8% compared to unsupplemented controls respectively. EGCG concentrations in the cellular media up to 20 µg/ml did not have any significant inhibitory effect on cell proliferation.

Figure 7:
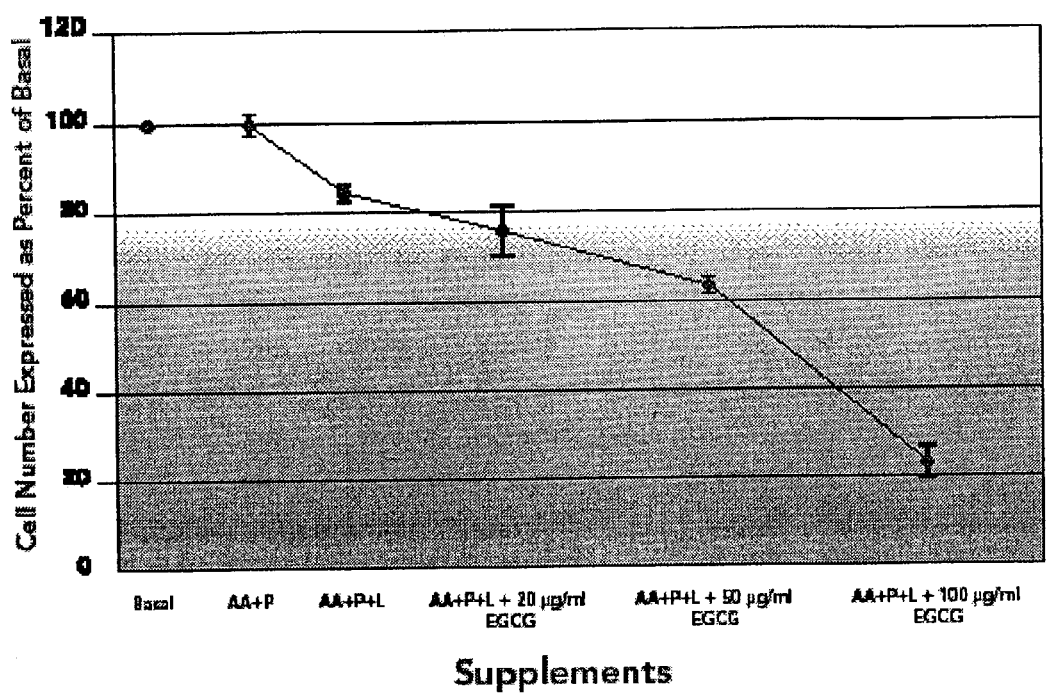
FIG. 7 depicts the effects of supplementation of basal medium with ascorbic acid, proline, lysine with various amounts of EGCG on cell proliferation of human breast cancer cells (MDA-MB 231).

We also studied the effects of ascorbic acid, lysine, proline and different concentrations of EGCG on proliferation of cancer cells. FIG. 7 shows non-significantly reduced the cell number to 86.1+1.93% with ascorbic acid, lysine and proline. Further addition of 20, 50 and 100 µg EGCG to this combination significantly reduced the cell number to 74±5.8, 64.8±1.6 and 22±5% compared to the control group respectively.

Colon Cancer HCT116 Cells

Figure 8:
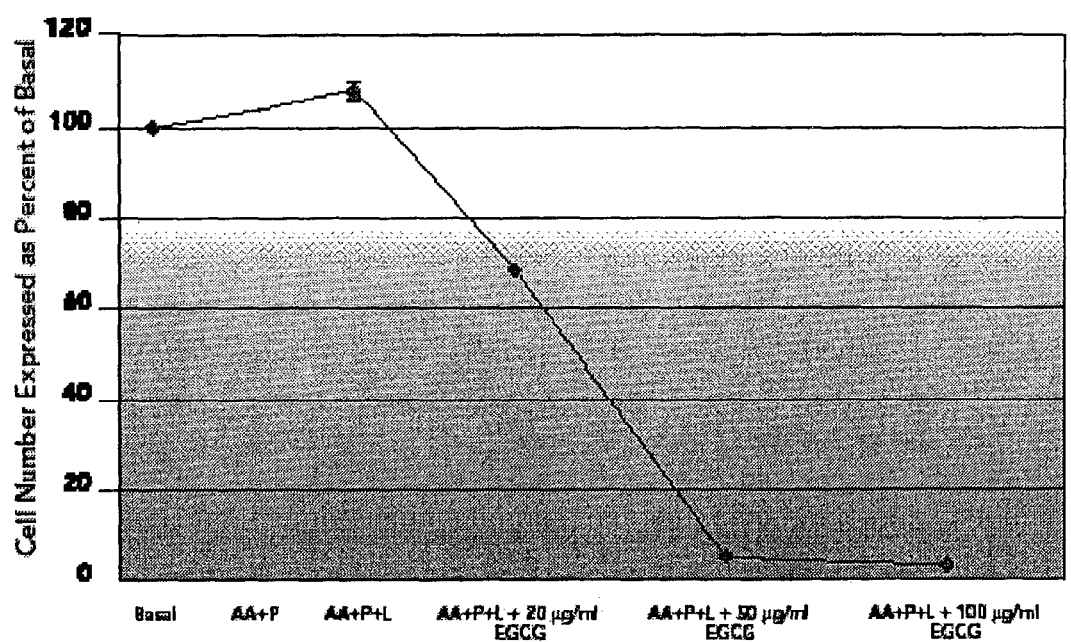
FIG. 8 depicts the effects of supplementation of basal medium with ascorbic acid, proline, lysine and various amounts of EGCG on cell proliferation of human colon cancer cells (HCT 116).

While the inhibitory effect of ascorbic acid, proline and lysine on cell proliferation of colon cancer cells was not pronounced, the combination of ascorbic acid, proline and lysine with 20 µg/ml EGCG significantly decreased the cell number to 69±0.5% (FIG. 8). A higher level of EGCG in this combination (50 µg/ml) drastically reduced the cell number to 4.6±0.3%. These data also show that the combined effects of ascorbic acid, proline and lysine in enhancing the anti-cancer activity of EGCG.

The anti-proliferative activity of the nutrient combinations used in these studies varied with the type of cancer cells. In breast cancer cells, the combination of ascorbic acid, proline and lysine with EGCG had higher anti-proliferative effects than when these nutrients were used individually. In melanoma and colon cancer cells exposed to the combination of ascorbic acid, proline, lysine did not affect their proliferation. However, combining these nutrients with 20 μg/ml EGCG resulted in a significant reduction in the number of colon cancer cells but not in melanoma cells. The colon cancer cells appeared to be more sensitive than the breast cancer cells and melanoma cells the least to the combination of ascorbic acid, proline, lysine and EGCG. The proliferation of the colon cancer cells was almost completely reduced (4.6%) when ascorbic acid, proline and lysine was given with 50 μg/ml of EGCG.

Example 6

Geltinase Zymograph Studies

Figure 9:
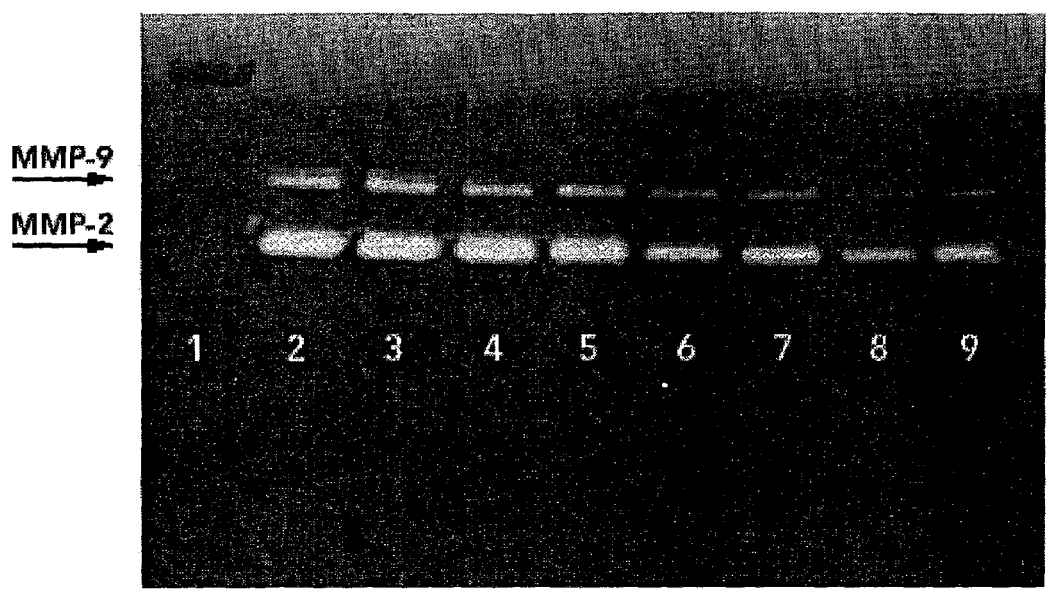
FIG. 9 depicts the effects of supplementation of basal medium with ascorbic acid, proline, lysine and various amounts of EGCG on expression of matrix metalloproteinases (MMP) in human melanoma cells.

The effect of EGCG on melanoma cells with basal and ascorbic acid, proline, and lysine supplementation on expression of MMPs is depicted in FIG. 9 by gelatinase zymography. Melanoma cells showed two bands corresponding to MMP-2 and MMP-9. Ascorbic acid, lysine and proline combination has no effect on the expression of MMPs bands as compared to the basal. However, EGCG inhibits the expression of both MMP-2 and MMP-9 in a dose dependent manner. The intensity of bands for basal and ascorbic acid, lysine and proline combination were the same. These data also show that the combined effects of ascorbic acid, proline and lysine in enhancing the anti-cancer activity (i.e., blocking the expression of MMPs) of EGCG.

Example 7

Extracellular Matrix Invasion and Migration Studies

The inhibitory effects of a combination of ascorbic acid, proline and lysine used separately and together with various concentrations of EGCG were examined. The effects of these combinations on extracellular matrix using pre-formed Matrigel matrices, routinely used to assess invasive potential of various cancer cell lines were studied.

Breast Cancer MDA-MB-231 Cells

Figure 10:
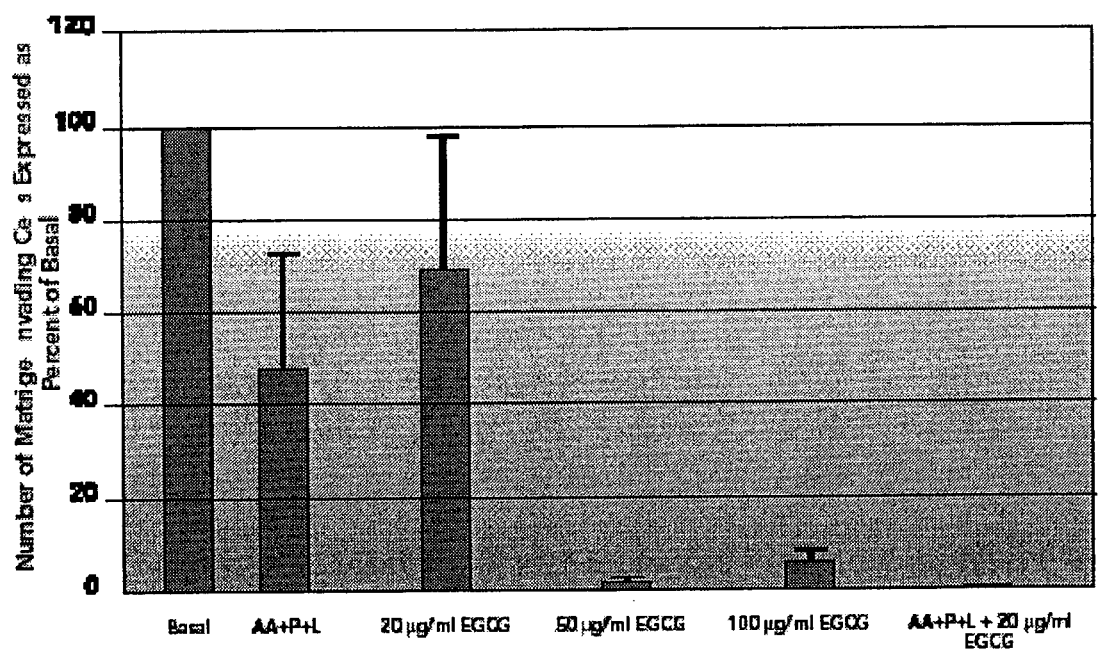
FIG. 10 depicts the effects of supplementation of basal medium with ascorbic acid, proline, lysine and various amounts of EGCG on Matrigel invasion by human breast cancer cells (MDA-MB 231).

FIG. 10 shows the results of Matrigel invasion of breast cancer cells incubated in the presence of ascorbic acid, proline and lysine. Invasion of cancer cells incubated in a combination of ascorbic acid, proline and lysine was reduced to 48.1±22.1% compared to cells incubated in non-supplemented media. In the media supplemented with 20 μg/ml of EGCG only, the number of invading cells decreased to 69.5±27.4%. The complete inhibition of matrix invasion by breast cancer cells was achieved in the presence of higher EGCG concentrations (50 μg/ml and 100 μg/ml). These data also show that the combined effects of ascorbic acid, proline and lysine in enhancing the anti-cancer activity of epigallocatechin gallate.

In another series of studies, supplementation of media with 100 μM ascorbic acid reduced the invasion by 36%. Supplementation with ascorbic acid and 140 μM proline further reduced the invasion by 47%. Using 400 μM lysine in addition to ascorbic acid and proline in the supplement further reduced the invasion to 67%; lysine shows a linear response in enhancing the effects of ascorbic acid and proline up to 800 μM level.

FIG. 10 also shows that the combination of ascorbic acid, proline and lysine as well as 20 μg/ml of EGCG was effective in a complete stopping of the invasion of cancer cells through the extracellular matrix. This combination made it possible to achieve the maximum inhibitory effect on cancer cells invasion without the necessity of using high concentrations of individual nutrients. As such, ascorbic acid, proline and lysine along with EGCG made it possible to stop matrix invasion of breast cancer cells completely at lower level of EGCG (20 μg/ml).

Colon Cancer HCT116 Cells

Figure 11:
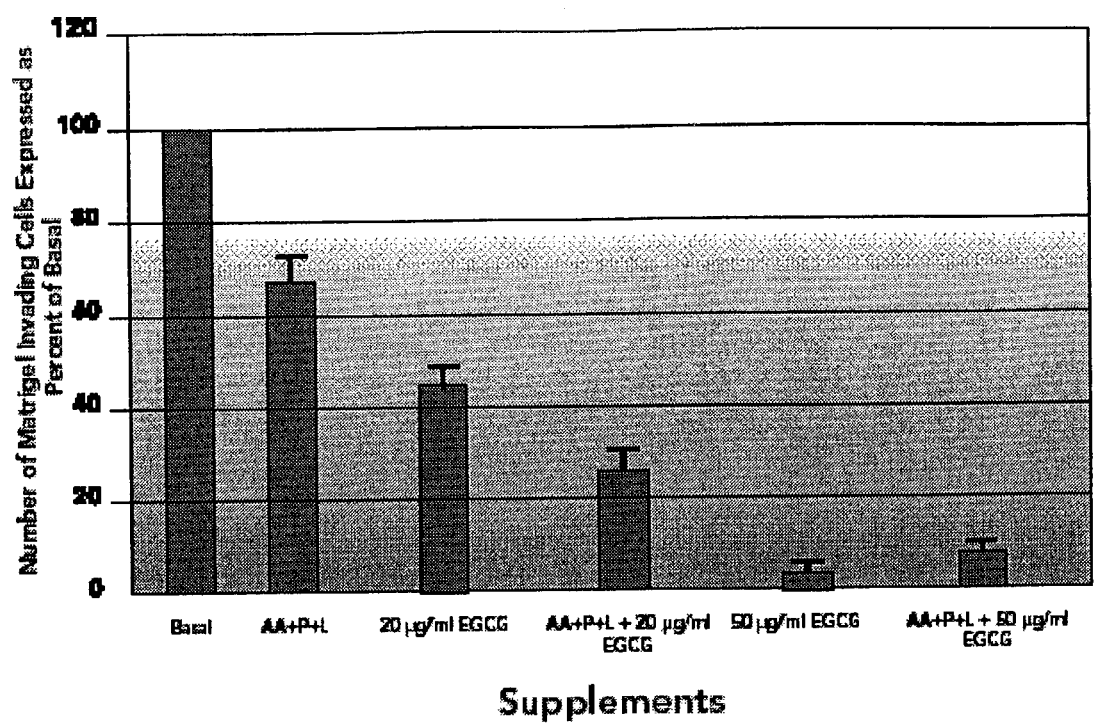
FIG. 11 depicts the effects of supplementation of basal medium with ascorbic acid, proline, lysine and various amounts of EGCG on Matrigel invasion by human colon cancer cells (HTC 116).

FIG. 11 shows that the combination of ascorbic acid, proline and lysine significantly reduced the invasion of colon cancer cells to 67.2±3.7%. The EGCG used alone at 20 μg/ml reduced the invasion to 44.9±3.3%, while the combination of ascorbic acid, proline and lysine and 20 μg/ml of EGCG had a synergistic effect reducing colon cancer cells invasion to 24.9±4.6%.

Melanoma A2058 Cells

Figure 12:
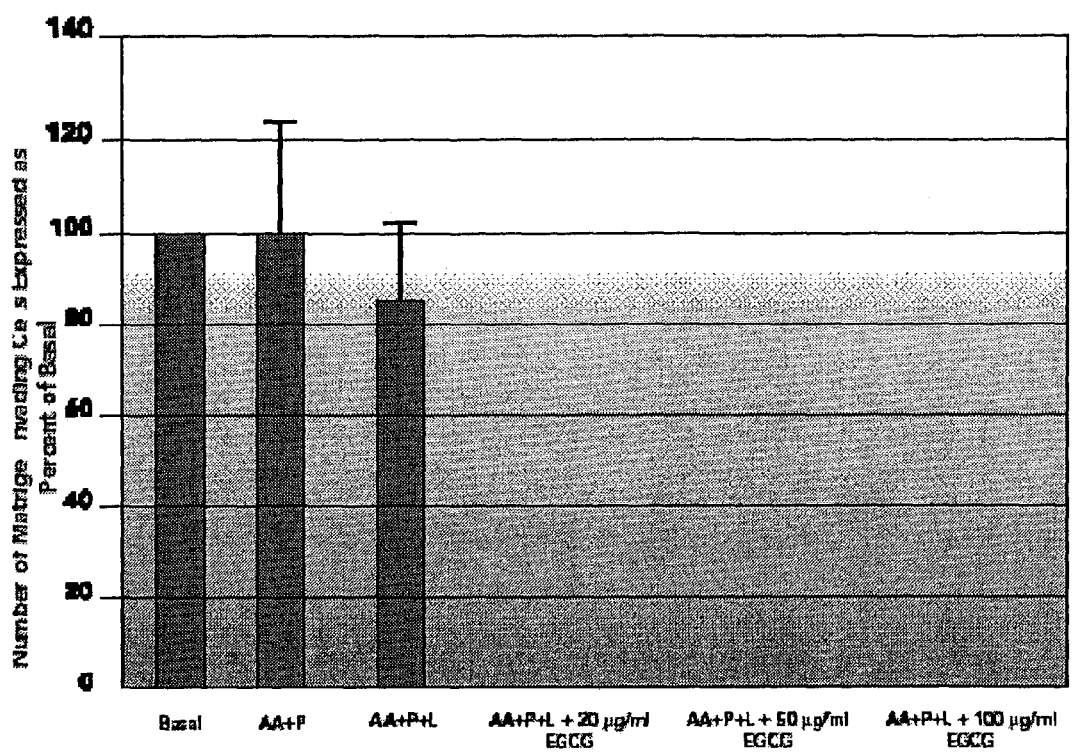
FIG. 12 depicts the effects of supplementation of basal medium with ascorbic acid, proline, lysine and various amounts of EGCG on reducing the number of invading cells in human melanoma cells (A 2058).

FIG. 12 shows that the combination of ascorbic acid, proline, and lysine was effective in reducing the number of invading cells to 88.2±4%, however this decrease was not statistically significant. Combining these nutrients with as little as 20 μg/ml of EGCG was effective in reducing the number of invading cells to zero.

The results show that the use of ascorbic acid, proline and lysine with EGCG enabled us to obtain drastic reduction in the number of cells invading and migrating through Matrigel membrane at lower levels of EGCG. The invasion was reduced to zero using as low a level as 20 μg/ml EGCG with ascorbic acid, proline and lysine in breast cancer cells and melanoma cells. The benefits of the combination results were not as spectacular with colon cancer cells as obtained with breast cancer cells. The level of EGCG had to be at 50 μg/ml to obtain 90% reduction in invasion by these cells. In this study, no alteration in MMPs expression in melanoma cells was observed, although EGCG has an inhibitory effect on their expression in a dose dependent fashion.

These series of studies conclusively demonstrate that the present nutrient pharmaceutical formulation comprising ascorbic acid, proline, lysine and at least one polyphenol compound exerts an effective anti-proliferative and anti-invasive effects on cancer cells.

Example 8

The following nutrient pharmaceutical formulations (Tables 1–5) and EPICAN FORTE™ (Table 6) are illustrated for their preparations. These formulations comprising ascorbic acid, proline, lysine and at least one polyphenol compound are found to be effective in blocking invasion of cancer cells and metastasis of cancer cells.

TABLE 1

Formulation 1

| Biochemical Substances | Amount | % |
| --- | --- | --- |
| Ascorbic Acid | 250 mg | 5.6 |
| Calcium Ascorbate | 250 mg | 5.6 |
| Magnesium Ascorbate | 250 mg | 5.6 |
| Ascorbyl Palmitate | 250 mg | 5.6 |
| Polyphenols | 1,000 mg | 22.5 |
| N-Acetyl-Cysteine | 200 mg | 4.5 |
| Lysine | 1,000 mg | 22.5 |
| Proline | 750 mg | 16.8 |
| Arginine | 500 mg | 11.2 |
| Selenium | 30 mcg | <0.01 |
| Copper | 2 mg | 0.04 |
| Manganese | 1 mg | 0.02 | mg = milligrams
mcg = micrograms
"%" refers to % weight of individual ingredient over total weight of formulation

TABLE 2

Formulation 2

| Biochemical Substances | Amount | % |
| --- | --- | --- |
| Ascorbic Acid | 25 mg | 5.7 |
| Calcium Ascorbate | 25 mg | 5.7 |
| Magnesium Ascorbate | 25 mg | 5.7 |
| Ascorbyl Palmitate | 25 mg | 5.7 |
| Polyphenols - 50% | 200 mg | 46.0 |
| N-Acetyl-Cysteine | 10 mg | 2.3 |
| Lysine | 50 mg | 11.5 |
| Proline | 25 mg | 5.7 |
| Arginine | 50 mg | 11.5 |
| Selenium | 1 mcg | <0.001 |
| Copper | 20 mcg | <0.001 |
| Manganese | 50 mcg | <0.001 | mg = milligrams
mcg = micrograms
"%" refers to % weight of individual ingredient over total weight of formulation

TABLE 3

Formulation 3

| Biochemical Substances | Amount | % |
| --- | --- | --- |
| Ascorbic Acid | 5,000 mg | 13.3 |
| Calcium Ascorbate | 5,000 mg | 13.3 |
| Magnesium Ascorbate | 5,000 mg | 13.3 |
| Ascorbyl Palmitate | 5,000 mg | 13.3 |
| Polyphenols - 100% | 5,000 mg | 13.3 |
| N-Acetyl-Cysteine | 1,500 mg | 4.0 |
| Lysine | 5,000 mg | 13.3 |
| Proline | 3,000 mg | 8.0 |
| Arginine | 3,000 mg | 8.0 |
| Selenium | 200 mcg | <0.001 |
| Copper | 9 mg | 0.02 |
| Manganese | 10 mg | 0.002 | mg = milligrams
mcg = micrograms
"%" refers to % weight of individual ingredient over total weight of formulation

TABLE 4

Formulation 4

| Biochemical Substances | Amount | % |
| --- | --- | --- |
| Ascorbic Acid | 250 mg | 4.7 |
| Calcium Ascorbate | 250 mg | 4.7 |
| Magnesium Ascorbate | 250 mg | 4.7 |
| Ascorbyl Palmitate | 250 mg | 4.7 |
| Polyphenols - 98% | 1,000 mg | 18.7 |
| N-Acetyl-Cysteine | 200 mg | 3.7 |
| Lysine | 1,000 mg | 18.7 |
| Proline | 750 mg | 14.0 |
| Arginine | 500 mg | 9.3 |
| Selenium | 100 mcg | <0.002 |
| Copper | 2 mg | 0.04 |
| Manganese | 1 mg | 0.02 |
| Calcium | 500 mg | 9.3 |
| Magnesium | 400 mg | 7.5 | mg = milligrams
mcg = micrograms
"%" refers to % weight of individual ingredient over total weight of formulation

TABLE 5

Formulation 5

| Biochemical Substances | Amount | % |
| --- | --- | --- |
| Ascorbic Acid | 250 mg | 4.5 |
| Calcium Ascorbate | 250 mg | 4.5 |
| Magnesium Ascorbate | 250 mg | 4.5 |
| Ascorbyl Palmitate | 250 mg | 4.5 |
| Polyphenols - 98% | 1,000 mg | 18 |
| N-Acetyl-Cysteine | 200 mg | 3.6 |
| Lysine | 1,000 mg | 18 |
| Proline | 750 mg | 13.5 |
| Arginine | 500 mg | 9 |
| Selenium | 100 mcg | <0.002 |
| Copper | 2 mg | <0.04 |
| Manganese | 1 mg | <0.02 |
| Calcium | 500 mg | 9 |
| Magnesium | 400 mg | 7.2 |
| Citrus Bioflavonoids | 200 mg | 3.6 | mg = milligrams
mcg = micrograms
"%" refers to % weight of individual ingredient over total weight of formulation.

TABLE 6

Formulation for EPICAN FORTE ™

Serving size: 6 Capsules (Suggested use: two capsules three times daily preferably with meals)

| 6 Capsules contain: | Amount per serving | % Daily Value |
| --- | --- | --- |
| L-Lysine | 1,000 mg | |
| L-Proline | 750 mg | |
| L-Arginine | 500 mg | |
| Vitamin C (as Ascorbic Acid, Calcium Ascorbate, Magnesium Ascorbate, and Ascorbate Palmitate) | 782 mg | 1180% |
| Calcium (from Calcium Ascorbate) | 22 mg | 2% |
| Magnesium (from Magnesium Ascorbate) | 50 mg | 12% |
| Standard Green Tea Extract (leaf) (80% polyphenol's—800 mg) decaffeinated | 1,000 mg | |
| N-Acetyl-Cysteine | 200 mg | |
| Selenium (from L-Selenomethionine) | 30 mg | 43% |
| Copper (from Copper Glycinate) | 2 mg | 100% |
| Manganese (from Manganese Citrate) | 1 mg | 50% | mg = milligrams
mcg = micrograms
EPICAN FORTE ™ is a trademark name under Matthias Rath, Inc. in a pending U.S. application.
Other ingredients: Vetetarian capsules (hydroxypropyl methylcellulose), silicon dioxide, cellulose and magnesium stearate.

Example 9

Effects of EPICAN FORTE™ on Human Cancer Cells

The effects EPICAN FORTE™ on human cancer cells were studied. Metastatic parameters such as expression of matrix metalloproteinases (MMPs) by gelatinase zymography, invasion potential through Matrigel and proliferation/growth by MTT assays were studied. The protocols for these assays are described in detail as above. Several human cancer cell lines were used: skin cancer—melanoma cells 2058, liver cancer—HepG2 cells, fibrosarcoma—HT 1080 cells, colon cancer—HCT 116, breast cancer ER+/−MCF-7 and breast cancer ER−/−MDA-MB-231.

The following tables (Tables 7 and 8) summarize the results:

TABLE 7

Effects of EPICAN FORTE ™ on Proliferation/Growth of Human Cancer Cell Lines:
Treatment Doses of EPICAN FORTE ™ (µg/ml): Percent of Control

| Cancer Cells | 0 | 10 | 50 | 100 | 500 | 1000 |
|---|---|---|---|---|---|---|
| Melanoma | 100% | 98 | — | 105 | — | 50 |
| Hep G2 | 100% | 92 | — | 138 | — | 85 |
| HT-1080 | 100% | 100 | — | 97 | 80 | 63 |
| Colon (HCT 116) | 100% | 119 | 125 | 141 | 120 | 106 |
| MCF-7 | 100% | 93 | 88 | 92 | 97 | 77 |
| MDA-MB-231 | 100% | 103 | — | 82 | — | 25 |

TABLE 8

Effects of EPICAN FORTE ™ on Matrigel Invasion and Migration by Human Cancer Cells:
Treatment Doses of EPICAN FORTE ™ (µg/ml): Percent Inhibition

| Cancer Cell | 0 | 10 | 50 | 100 | 500 | 1000 |
|---|---|---|---|---|---|---|
| Melanoma | 0% | 80 | 98 | 100 | — | — |
| HepG2 | 0% | 15 | 25 | 50 | 95 | 100 |
| HT-1080 | 0% | 90 | — | 50 | 70 | 100 |
| Colon (HCT 116) | 0% | 20 | 50 | 80 | 100 | — |
| MDA-MB-231 | 0% | 50 | — | 98 | — | — |
| MCF-7 | | | | Non-invasive | | |

Effects of EPICAN FORTE™ on the Expression of Matrix Metalloproteinases (MMPs) by Human Cancer Cell Lines:

Melanoma Cells: Melanoma cells exhibited two bands on gelatinase zymography corresponding to MMP-2 and MMP-9. EPICAN FORTE™ inhibited the expression of MMP-2 and -9 in a dose dependent fashion. The expression of MMP-2 and -9 was significantly inhibited with a concentration of 100 µg/ml of EPICAN FORTE™ and virtually undetectable with a concentration of 1000 µg/ml.

HepG2 Cells: Like melanoma cell, HepG2 cell also expressed two bands corresponding to MMP-2 and MMP-9. EPICAN FORTE™ inhibited the expression of MMP-2 and -9 at 500 and 1000 µg/ml concentration.

Fibrosarcoma HT-1080: HT-1080 cells exhibited two bands for MMP-2 and -9. EPICAN FORTE™ also inhibited the expression of both the bands in a dose dependent fashion. Very faint bands were seen at 500 and 1000 µg/ml concentration.

Colon cancer HCT116: Colon cancer cells showed only one band on zymography corresponding to MMP-2 which totally disappeared at 100 µg/ml concentration.

MCF-7 and MDA-MB-231: These cancer cell lines did not any MMPs bands under our experimental concentration, which were similar to the other cancer cell lines.

Invasion of MDA-MB-231 through Matrigel was inhibited by 50, 60 and 95% by 10, 50 and 100 µg/ml of EPICAN FORTE™ respectively. EPICAN FORTE™ was not toxic to MDA-MB-231 at 10 µg/ml, showed slight toxicity at 100 µg/ml. However, it exhibited significant toxicity at 1000 µg/ml. Neither MMP-2 nor MMP-9 was expressed by zymography. In contrast, EPICAN FORTE™ was not toxic to MCF-7 even at 500 µg/ml, and exhibited slight toxicity at 1000 µg/ml. MCF-7 was not invasive and did not express MMPs activities.

EPICAN FORTE™ inhibits the expression of MMP-2 and MMP-9 in a dose-dependent fashion. The expression of MMP-2 and MMP-9 was significantly inhibited with a concentration of 100 µg/ml of EPICAN FORTE™ and virtually undetectable with a concentration of 100 µg/ml. EPICAN FORTE™ used at 10 and 100 µg/ml concentrations did not significantly affect the cells viability, and at 100 µg/ml it showed cytotoxicity at the range of 10–40 percent, depending on cell type. The invasion of melanoma cells, MDA-MB-23 1 cells, and a co-culture of melanoma cells with NHDF through Matrigel was significantly reduced in a dose-dependent manner. Invasion of HT-1080 cells thought Matrigel was inhibited by 10%, 50%, 70% and 100% at 10, 100, 200 and 1000 µg/ml respectively. Interestingly, EPICAN FORTE™ was not toxic to HT-1080 cells at 100 µg/ml. These results demonstrate that EPICAN FORTE™ is very effective for several cancer cell lines and also in co-culture. These observations reveal that EPICAN FORTE™ may provide a natural therapeutic basis that makes it a valuable and promising candidate for the treatment of human cancers.

Example 10

Effects of EPICAN FORTE™ on Human Normal Cell Lines

The effects of EPICAN FORTE™ on normal human cells was studied. Parameters similar to those of cancer cell lines were employed; namely zymography for MMPs expression, invasion through Matrigel and proliferation/growth by MTT assays. Several normal human dermal fibroblast (NHDF) were used, including: human chondrocytes and human stromal cells.

The following tables (Tables 9 and 10) summarize the effects of EPICAN FORTE™ on proliferation/growth and metastasis invasion in normal human cells:

TABLE 9

Effects of EPICAN FORTE ™ on Proliferation/Growth of Normal Human Cells. Treatment Doses of EPICAN FORTE ™ (µg/ml): Percent of Control

| Normal Cells | 0 | 10 | 50 | 100 | 500 | 100 |
|---|---|---|---|---|---|---|
| NHDF | 100% | 118 | — | 135 | — | 90 |
| Chondrocytes | 100% | 113 | — | 148 | 76 | 82 |
| Stromal Cells | 100% | 100 | 116 | 115 | 98 | 64 |

TABLE 10

Effects of EPICAN FORTE ™ on Matrigel Invasion by Normal Human Cells. Treatment Doses of EPICAN FORTE ™ (µg/ml): Percent Inhibition

| Normal Cell | 0 | 10 | 50 | 100 | 200 | 1000 |
|---|---|---|---|---|---|---|
| NHDF | 0% | 67% | 89% | 100% | — | — |
| Chondrocytes | 0% | 45% | 85% | 95% | 100% | — |
| Stromal Cells | 0% | 0% | — | 95% | 100% | |

The effects of EPICAN FORTE™ on the expression of matrix metalloproteinases (MMPs) by normal human cells are summarized as followed:

NHDF: NHDF expressed only one band on zymography corresponding to MMP-2, which virtually disappeared at 1000 µg/ml concentration of EPICAN FORTE™.

Chondrocytes: Chondrocytes also showed only one band corresponding to MMP-2. EPICAN FORTE™ inhibited the expression of MMP-2 in a dose dependent manner. The expression of MMP-2 was significantly inhibited at a concentration of 100 µg/ml of EPICAN FORTE™ and totally disappeared at 200 µg/ml concentration of EPICAN FORTE™.

Stromal Cells: Stromal cells also exhibited only one band corresponding to MMP-2. EPICAN FORTE™ inhibited the expression of MMP-2 in a dose dependent fashion. Very faint band was seen at 50 and 100 µg/ml concentration which was undetected at 200 and 500 µg/ml concentration.

In summary, the results indicated that EPICAN FORTE™ inhibits the expression of MMP-2 in a dose-dependent manner. The expression of MMP-2 was significantly inhibited at a concentration of 100 µg/ml of EPICAN FORTE™ and virtually not detected at a concentration of 200 µg/ml. In addition, it was also found that invasion of chondrocytes through Matrigel was inhibited by 50%, 85% and 95% at 10 µg/ml, 100 µg/ml and 200 µg/ml. At 500 µg/ml the invasion was totally reduced to 0%.

EPICAN FORTE™ was not toxic to chrondrocytes even at a concentration of 200 µg/ml. In fact, EPICAN FORTE™ exerted a cell proliferation effect, a 70% increase in cell proliferation with 200 µg/ml, 70% more over the control. Slight toxic effect was seen only at 500 µg/ml. These results demonstrate that EPICAN FORTE™ is effective in inhibiting the MMP-2 expression and that EPICAN FORTE™ represents a novel anti-inflammatory nutrient formulation as a natural approach to inhibit MMP production and extracellular matrix degradation in osteoarthritis and other related disorders including excessive cartilage degradation.

Example 11

Female patient was diagnosed with Gliablastoma after suffering a facial stroke characterized by numbness of lips and the left side of the face. MR scans (FIG. 13; left diagram) revealed a brain tumor on the left side of the brain as shown in the left scan. Patient was treated with radiation treatment. Side effect included falling out of the hair. Patient also took cortisone, which resulted in water retention and bloating and an eventual weight gain of approximately 20 kg. Follow up MR scans revealed that despite the treatments, there was no reduction in the size of the tumor. Prognosis by treating physicians was eventual death as a result of continued tumor growth.

On Apr. 10, 2002, patient started oral administration of the EPICAN FORTE™ formula. Dosage was between 6–9 capsules per day. Patient then discontinued taking cortisone and lost over 20 kg. Patient continued the EPICAN FORTE™ treatment for approximately 5 months. MR scan (FIG. 13; right diagram) of the patient brain in August of 2002 could no longer detect the brain tumor.

Example 12

Male patient was found to have a markedly elevated level (59.9 µg/l) of the tumor marker PSA and was diagnosed with prostate cancer. The X-ray CT scan revealed metastasis along the lymphatic vessels of the aorta (FIG. 14; left diagram).

After diagnosis started oral administration of the EPICAN FORTE™ formula. Dosage was between 6–9 capsules per day. After approximately three months of treatment with EPICAN FORTE™, the patient's PSA level fell from 59.9 µg/l to 0.9 µg/l.

On Oct. 23, 2002, approximately 5 months from initiating administration of the EPICAN FORTE™ formula, the patient was given a follow up CT scan. The previously visible lymphatic metastasis was no longer detectable (right diagram), and the patient's prostate returned to normal size.

A number of embodiments of the invention have been described. Nevertheless, it will be understood that various modifications may be made without departing from the spirit and scope of the invention.

What is claimed is:

1. A method for treating cancer selected from the group consisting of melanoma cancer, breast cancer, colon cancer, lung cancer and brain cancer, and prostrate cancer in an individual, comprising the step of administering to the individual the nutrient pharmaceutical composition comprising (a) an ascorbic compound; (b) a combination of amino acids and amino acid derivatives consisting of L-lysine L-proline and N-acetyl cysteine; and (c) at least one polyphenol compound selected from the group consisting of epigallocatechin gallate, epicatechin gallate, epigallocatechin, epicatechin, and catechin,
   wherein the compounds of (a) and (b) enhance the polyphenol compound's activity in blocking cancer proliferation and metastasis.

2. The method of claim 1 wherein the cancer is selected from the group consisting of melanoma cancer, breast cancer, colon cancer, lung cancer and brain cancer.

* * * * *